(12) United States Patent
Séguin

(10) Patent No.: US 7,288,097 B2
(45) Date of Patent: Oct. 30, 2007

(54) SURGICAL DEVICE FOR CONNECTING SOFT TISSUE

(75) Inventor: Jacques Séguin, Paris (FR)

(73) Assignee: Evalve, Inc., Menlo Park, CA (US)

( * ) Notice: Subject to any disclaimer, the term of this patent is extended or adjusted under 35 U.S.C. 154(b) by 247 days.

(21) Appl. No.: 10/877,279

(22) Filed: Jun. 24, 2004

(65) Prior Publication Data
US 2004/0236354 A1   Nov. 25, 2004

Related U.S. Application Data

(60) Division of application No. 10/202,599, filed on Jul. 24, 2002, now Pat. No. 6,770,083, which is a division of application No. 09/523,018, which is a continuation of application No. PCT/FR98/01960, filed on Sep. 14, 1998, now Pat. No. 6,461,366.

(51) Int. Cl.
*A61B 17/10* (2006.01)

(52) U.S. Cl. ..................................... 606/142

(58) Field of Classification Search ............... 606/142, 606/139, 144, 151, 157, 148, 143, 185, 42
See application file for complete search history.

(56) References Cited

U.S. PATENT DOCUMENTS

| | | | |
|---|---|---|---|
| 2,108,206 | A | 2/1938 | Meeker |
| 3,378,010 | A | 4/1968 | Codling et al. |
| 3,761,979 | A | 10/1973 | Moulopoulos |
| 3,874,338 | A | 4/1975 | Happel |
| 4,056,854 | A | 11/1977 | Boretos et al. |
| 4,297,749 | A | 11/1981 | Davis et al. |
| 4,484,579 | A | 11/1984 | Meno et al. |
| 4,641,366 | A | 2/1987 | Yokoyama et al. |
| 4,809,695 | A | 3/1989 | Gwathmey et al. |
| 4,917,089 | A | 4/1990 | Sideris |

(Continued)

FOREIGN PATENT DOCUMENTS

DE   3504292   2/1985

(Continued)

OTHER PUBLICATIONS

Abe et al., "De Vega's annuloplasty for acquired tricuspid disease: Early and late results in 110 patients" Ann. Thorac. Surg. (1989) 48:670-676.

(Continued)

*Primary Examiner*—Kevin T. Truong
(74) *Attorney, Agent, or Firm*—Townsend and Townsend and Crew LLP

(57) ABSTRACT

The invention comprises a surgical instrument including an external tube (2) and two elongated members (4) positioned in said tube (2), each of which includes a distal end (10*a*) for capturing one of the two tissue zones (M1, M2) to be attached. The instrument (1) may further comprise a catching member (22, 25) for each tissue (M1, M2) to be attached; a rod (15, 16) linked to each catching member (22, 25) enabling tension to move axially, said rod (15, 16) being separable from said catching member (22, 25) when a tension is exerted on it beyond a certain threshold; and a member (17*a*) forming a stop for locking axially each catching member (22, 25) during said tension.

7 Claims, 4 Drawing Sheets

U.S. PATENT DOCUMENTS

| | | |
|---|---|---|
| 4,994,077 A | 2/1991 | Dobben |
| 5,042,707 A | 8/1991 | Taheri |
| 5,049,153 A | 9/1991 | Nakao et al. |
| 5,069,679 A | 12/1991 | Taheri |
| 5,171,252 A | 12/1992 | Friedland |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,250,071 A | 10/1993 | Palermo |
| 5,254,130 A | 10/1993 | Poncet et al. |
| 5,261,916 A | 11/1993 | Engelson |
| 5,312,415 A | 5/1994 | Palermo |
| 5,332,402 A | 7/1994 | Teitelbaum |
| 5,350,397 A | 9/1994 | Palermo et al. |
| 5,383,886 A | 1/1995 | Kensey et al. |
| 5,403,326 A | 4/1995 | Harrison et al. |
| 5,411,552 A | 5/1995 | Andersen et al. |
| 5,417,700 A | 5/1995 | Egan |
| 5,423,858 A | 6/1995 | Bolanos et al. |
| 5,423,882 A | 6/1995 | Jackman et al. |
| 5,450,860 A | 9/1995 | O'Connor |
| 5,478,309 A | 12/1995 | Sweezer et al. |
| 5,478,353 A | 12/1995 | Yoon |
| 5,520,701 A | 5/1996 | Lerch |
| 5,522,873 A | 6/1996 | Jackman et al. |
| 5,536,251 A | 7/1996 | Evard et al. |
| 5,542,949 A | 8/1996 | Yoon |
| 5,554,185 A | 9/1996 | Block et al. |
| 5,571,137 A | 11/1996 | Marlow et al. |
| 5,571,215 A | 11/1996 | Sterman et al. |
| 5,618,306 A | 4/1997 | Roth et al. |
| 5,634,932 A | 6/1997 | Schmidt |
| 5,640,955 A | 6/1997 | Ockuly et al. |
| 5,690,671 A | 11/1997 | McGurk et al. |
| 5,695,504 A * | 12/1997 | Gifford et al. .............. 606/153 |
| 5,713,910 A | 2/1998 | Gordon et al. |
| 5,716,367 A | 2/1998 | Koike et al. |
| 5,718,725 A | 2/1998 | Sterman et al. |
| 5,719,725 A | 2/1998 | Nakao |
| 5,741,280 A | 4/1998 | Fleenor |
| 5,769,812 A | 6/1998 | Stevens et al. |
| 5,797,927 A | 8/1998 | Yoon |
| 5,797,960 A | 8/1998 | Stevens et al. |
| 5,810,847 A | 9/1998 | Laufer et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,855,614 A | 1/1999 | Stevens et al. |
| 5,879,307 A | 3/1999 | Chio et al. |
| 5,885,271 A | 3/1999 | Hamilton et al. |
| 5,916,147 A | 6/1999 | Boury |
| 5,928,224 A | 7/1999 | Laufer |
| 5,947,363 A | 9/1999 | Bolduc et al. |
| 5,954,732 A | 9/1999 | Hart et al. |
| 5,980,455 A | 11/1999 | Daniel et al. |
| 5,989,284 A | 11/1999 | Laufer |
| 6,019,722 A | 2/2000 | Spence et al. |
| 6,077,214 A | 6/2000 | Mortier et al. |
| 6,117,144 A | 9/2000 | Nobles et al. |
| 6,132,447 A | 10/2000 | Dorsey |
| 6,143,024 A | 11/2000 | Campbell et al. |
| 6,165,183 A | 12/2000 | Kuehn et al. |
| 6,190,408 B1 | 2/2001 | Melvin |
| 6,210,432 B1 | 4/2001 | Solem et al. |
| 6,269,819 B1 | 8/2001 | Oz et al. |
| 6,299,637 B1 | 10/2001 | Shaolian et al. |
| 6,306,133 B1 | 10/2001 | Tu et al. |
| 6,332,893 B1 | 12/2001 | Mortier et al. |
| 6,355,030 B1 | 3/2002 | Aldrich et al. |
| 6,402,781 B1 | 6/2002 | Langberg et al. |
| 6,406,420 B1 | 6/2002 | McCarthy et al. |
| 6,537,314 B2 | 3/2003 | Langberg et al. |
| 6,562,037 B2 | 5/2003 | Paton et al. |
| 6,575,971 B2 | 6/2003 | Hauck et al. |
| 6,585,761 B2 | 7/2003 | Taheri |
| 6,619,291 B2 | 9/2003 | Hlavka et al. |
| 6,626,899 B2 | 9/2003 | Houser et al. |
| 6,626,930 B1 | 9/2003 | Allen et al. |
| 6,656,221 B2 | 12/2003 | Taylor et al. |
| 6,689,164 B1 | 2/2004 | Seguin |
| 6,701,929 B2 | 3/2004 | Hussein |
| 6,702,826 B2 | 3/2004 | Liddicoat et al. |
| 6,709,382 B1 | 3/2004 | Horner |
| 6,709,456 B2 | 3/2004 | Langberg et al. |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,755,777 B2 | 6/2004 | Schweich et al. |
| 6,764,510 B2 | 7/2004 | Vidlund et al. |
| 6,770,083 B2 | 8/2004 | Seguin |
| 6,797,001 B2 | 9/2004 | Mathis et al. |
| 6,797,002 B2 | 9/2004 | Spence et al. |
| 6,875,224 B2 | 4/2005 | Grimes |
| 6,945,978 B1 | 9/2005 | Hyde |
| 6,949,122 B2 | 9/2005 | Adams et al. |
| 7,011,669 B2 * | 3/2006 | Kimblad .................. 606/151 |
| 7,112,207 B2 | 9/2006 | Allen et al. |
| 2002/0013571 A1 | 1/2002 | Goldfarb et al. |
| 2002/0035381 A1 | 3/2002 | Houser et al. |
| 2002/0087148 A1 | 7/2002 | Brock et al. |
| 2002/0087169 A1 | 7/2002 | Brock et al. |
| 2002/0156526 A1 | 10/2002 | Hlavka et al. |
| 2002/0161378 A1 | 10/2002 | Downing |
| 2002/0169360 A1 | 11/2002 | Taylor et al. |
| 2002/0183766 A1 | 12/2002 | Seguin |
| 2003/0050693 A1 | 3/2003 | Quijano et al. |
| 2003/0069570 A1 | 4/2003 | Witzel et al. |
| 2003/0069593 A1 | 4/2003 | Tremulls et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0120341 A1 | 6/2003 | Shennib et al. |
| 2003/0130730 A1 | 7/2003 | Cohn et al. |
| 2003/0167071 A1 | 9/2003 | Martin et al. |
| 2003/0187467 A1 | 10/2003 | Schreck |
| 2003/0229395 A1 | 12/2003 | Cox |
| 2003/0233038 A1 | 12/2003 | Hassett |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al |
| 2004/0049211 A1 | 3/2004 | Tremulis et al. |
| 2004/0073302 A1 | 4/2004 | Rourke et al. |
| 2004/0088047 A1 | 5/2004 | Spence et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |

| | | | |
|---|---|---|---|
| 2004/0133063 A1 | 7/2004 | McCarthy et al. | |
| 2004/0133192 A1 | 7/2004 | Houser et al. | |
| 2004/0133220 A1 | 7/2004 | Lashinski et al. | |
| 2004/0133240 A1 | 7/2004 | Adams et al. | |
| 2004/0133273 A1 | 7/2004 | Cox | |
| 2004/0138744 A1 | 7/2004 | Lashinski et al. | |
| 2004/0138745 A1 | 7/2004 | Macoviak et al. | |
| 2004/0148021 A1 | 7/2004 | Cartledge et al. | |
| 2004/0152947 A1 | 8/2004 | Schroeder et al. | |
| 2004/0153144 A1 | 8/2004 | Seguin | |
| 2004/0158123 A1 | 8/2004 | Jayaraman | |
| 2004/0162610 A1 | 8/2004 | Lalska et al. | |
| 2004/0167539 A1 | 8/2004 | Kuehn et al. | |
| 2004/0193191 A1 | 9/2004 | Starksen et al. | |
| 2004/0215339 A1 | 10/2004 | Dresler et al. | |
| 2004/0220593 A1 | 11/2004 | Greenhalgh | |
| 2004/0220657 A1 | 11/2004 | Nieminen et al. | |
| 2004/0225300 A1 | 11/2004 | Goldfarb et al. | |
| 2004/0236354 A1 | 11/2004 | Seguin | |
| 2004/0243229 A1 | 12/2004 | Vidlund et al. | |
| 2004/0249452 A1 | 12/2004 | Adams et al. | |
| 2004/0249453 A1 | 12/2004 | Cartledge et al. | |
| 2005/0004583 A1 | 1/2005 | Oz et al. | |
| 2005/0004668 A1 | 1/2005 | Aklog et al. | |
| 2005/0021057 A1 | 1/2005 | St. Goar et al. | |
| 2005/0021058 A1 | 1/2005 | St. Goar et al. | |
| 2005/0033446 A1 | 2/2005 | Deem et al. | |
| 2005/0038508 A1 | 2/2005 | Gabbay | |
| 2005/0049698 A1 | 3/2005 | Bolling et al. | |
| 2005/0055089 A1 | 3/2005 | Macoviak et al. | |
| 2005/0059351 A1 | 3/2005 | Cauwels et al. | |
| 2005/0149014 A1 | 7/2005 | Hauck et al. | |
| 2005/0159810 A1 | 7/2005 | Filsoufi | |
| 2005/0197694 A1 | 9/2005 | Pai et al. | |
| 2005/0197695 A1 | 9/2005 | Stacchino et al. | |
| 2005/0216039 A1 | 9/2005 | Lederman | |
| 2005/0228422 A1 | 10/2005 | Machold et al. | |
| 2005/0228495 A1 | 10/2005 | Macoviak | |
| 2005/0251001 A1 | 11/2005 | Hassett | |
| 2005/0273160 A1 | 12/2005 | Lashinski et al. | |
| 2005/0287493 A1 | 12/2005 | Schreck et al. | |
| 2006/0058871 A1 | 3/2006 | Zakay et al. | |
| 2006/0195012 A1 | 8/2006 | Mortler et al. | |
| 2006/0252984 A1 | 11/2006 | Rahdert et al. | |

FOREIGN PATENT DOCUMENTS

| | | |
|---|---|---|
| EP | 0179562 | 7/1989 |
| EP | 0558031 | 2/1993 |
| EP | 0684012 A2 | 11/1995 |
| EP | 0684012 A3 | 11/1995 |
| EP | 0684012 B1 | 11/1995 |
| GB | 1598111 | 9/1981 |
| GB | 2151142 | 11/1984 |
| JP | 11089937 | 4/1999 |
| WO | WO 81/00668 | 3/1981 |
| WO | WO 91/01689 | 2/1991 |
| WO | WO 91/18881 | 12/1991 |
| WO | WO 92/12690 | 8/1992 |
| WO | WO 94/18881 | 9/1994 |
| WO | WO 94/18893 | 9/1994 |
| WO | WO 97/39688 | 10/1997 |
| WO | WO 98/07375 | 2/1998 |
| WO | WO 98/30153 | 7/1998 |
| WO | WO 98/35638 | 8/1998 |
| WO | WO 99/00059 | 1/1999 |
| WO | WO 99/01377 | 1/1999 |
| WO | WO 99/07354 | 2/1999 |
| WO | WO 00/03759 | 1/2000 |
| WO | WO 00/60995 | 10/2000 |
| WO | WO 01/26557 | 4/2001 |
| WO | WO 01/26586 | 4/2001 |
| WO | WO 01/28432 | 4/2001 |
| WO | WO 02/03892 | 1/2002 |
| WO | WO 03/001893 | 1/2003 |
| WO | WO 03/020179 | 3/2003 |
| WO | WO 03/028558 | 4/2003 |
| WO | WO 03/037171 | 5/2003 |
| WO | WO 03/047467 | 6/2003 |
| WO | WO 03/049619 | 6/2003 |
| WO | WO 03/073910 | 9/2003 |
| WO | WO 03/073913 | 9/2003 |
| WO | WO 00/59382 A1 | 10/2003 |
| WO | WO 03/105667 A3 | 12/2003 |
| WO | WO 2004/004607 | 1/2004 |
| WO | WO 2004/012583 | 2/2004 |
| WO | WO 04/082538 A2 | 3/2004 |
| WO | WO 2004/019811 | 3/2004 |
| WO | WO 2004/030570 | 4/2004 |
| WO | WO 2004/037317 | 5/2004 |
| WO | WO 04/045378 A2 | 6/2004 |
| WO | WO 2004/045370 | 6/2004 |
| WO | WO 2004/045463 | 6/2004 |
| WO | WO 2004/047679 | 6/2004 |
| WO | WO 2004/062725 | 7/2004 |
| WO | WO 04/082523 A2 | 9/2004 |
| WO | WO 2004/093730 | 11/2004 |
| WO | WO 2004/112585 | 12/2004 |
| WO | WO 2004/112651 | 12/2004 |
| WO | WO 2005/002424 | 1/2005 |
| WO | WO 05/027797 A1 | 3/2005 |
| WO | WO 2005/018507 | 3/2005 |
| WO | WO 05/032421 A2 | 4/2005 |
| WO | WO 05/062931 A2 | 7/2005 |
| WO | WO 2005/112792 | 12/2005 |
| WO | WO 2006/105008 | 10/2006 |
| WO | WO 2006/105009 | 10/2006 |
| WO | WO 2006/115875 | 11/2006 |
| WO | WO 2006/115876 | 11/2006 |

OTHER PUBLICATIONS

Abe et al., "Updated: De Vega's annuloplasty for acquired tricuspid disease: Early and late results in 110 patients" Ann. Thorac. Surg. (1996) 62: 1876-1877.

Alvarez et al., "Repairing the degenerative mitral valve: Ten- to fifteen-year follow-up" J. Thoracic. Cardiovasc. Surg. (1996) 112:238-247.

Bach et al., "Early improvement in congestive heart failure after correction of secondary mitral regurgitation in end-stage cardiomyopathy" Am. Heart J. (1995) 129:1165-1170.

Bach et al., "Improvement following correction of secondary mitral regurgitation in end-stage cardiomyopathy with mitral annuloplasty" Am. J. Cardiol. (1996) 78:966-969.

Bailey, Surgery of the Heart, Chapter 20, 1995, pp. 686-737.

Bolling et al., "Surgery for acquired heart disease" (1995) 109:676-683.

Dec et al., "Idiopathic dilated cardiomyopathy" N. Engl. J. Med. (1994) 331:1564-1575.

Fucci et al., "Improved results with mitral valve repair using new surgical techniques" Eur. J. Cardiothorac. Surg. (1995) 9:621-627 (Medline Record enclosed herewith).

Kameda et al., "Annuloplasty for severe mitral regurgitation to dilated cardiomyopathy" Am. Thorac. Surg. (1996) 61:1829-1832.

Khan et al., "Blade atrial septostomy: Experience with first 50 procedures" Cathet. Cardiovasc. Diagn. (1991) 23:257-262.

Maisano et al., "The edge-to-edge technique: A simplified method to correct mitral insufficiency" Eur. J. Cardiothorac. Surg. (1998) 13:240-246.

McCarthy et al., "Tricuspid valve repair with the Cosgrove-Edwards annuloplasty system" Am. Thorac. Surg. (1997) 64:267-268.

Park et al., "Clinical use of a blade atrial septostomy" Circulation (1978) 58:600-608.

Reul, Ross M. and Cohn, Lawrence II, Mitral Valve Reconstruction for Mitral Insufficiency, Progress in Cardiovascular Diseases, No. 6, May/Jun. 1997, pp. 567-599, vol. XXXIX.

Ricchi et al., "Linear segmental annuloplasty for mitral valve repair" Ann. Thorac. Surg. (1997) 63:1805-1806.

Tager et al., "Long-term follow-up of Rheumatic patients undergoing left-sided valve replacement with tricuspid annuloplasty -Validityof preoperative echocardiographic criteria in the decision to perform tricuspid annuloplasty" Am. J. Cardiol. (1998) 81:1013-1016.

Uchida et al., "Percutaneous cardiomyotomy and valvultomy with angioscopic guidance" Am. Heart J. (1991) 121:1221-1224.

Umana et al., "Bow-tie mitral valve repair successfully addresses subvalvular dysfunction in ischemic mitral regurgitation" (1997) Surgical Forum pp. 279-280.

Umana et al., "Bow-tie mitral valve repair: An adjuvant technique for ischemic mitral regurgitation" Ann. Thorac. Surg. (1998) 66:1640-1646.

Bernal et al., "The 'Valve Racket': a new and different concept of atrioventricular valve repair," Eur. J. Cardio-thoracic Surgery 29:1026-29 (2006).

Derwent citing German language patent EP 684012 published Nov. 12, 1995 for: "Thread for constructing surgical seam has flexible section with two ends, with lower fastening part on thread first end having hollow cylinder with continuous hole through which surgical needle threads" 2 pgs.

Derwent citing Japanese language patent JP 11089937 published Jun. 4, 1999 for: "Catheter for mitral regurgitation test—includes jet nozzles provided on rear side of large diametered spindle shaped portion attached to end of narrow diametered tube" 1 pg.

Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).

Langer et al., "Posterior mitral leaflet extensions: An adjunctive repair option for ischemic mitral regurgitation?," J. Thorac. Cardiovasc. Surf. 131:868-77 (2006).

* cited by examiner

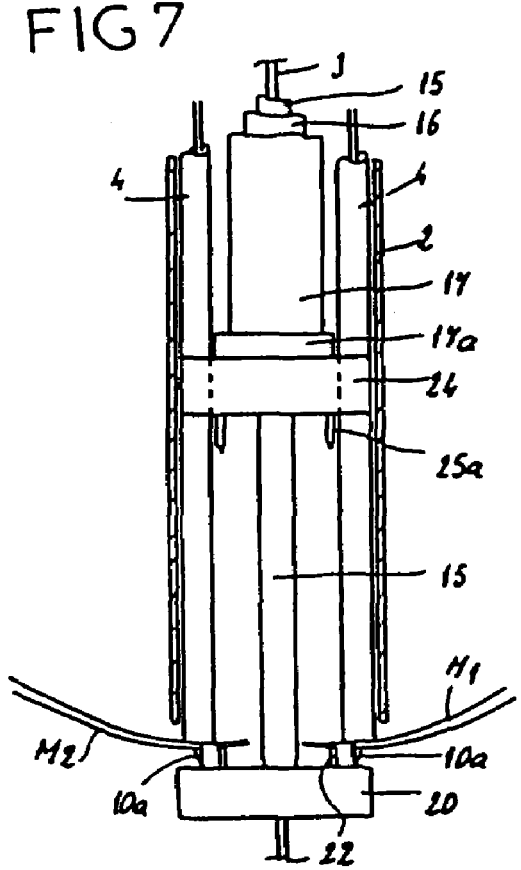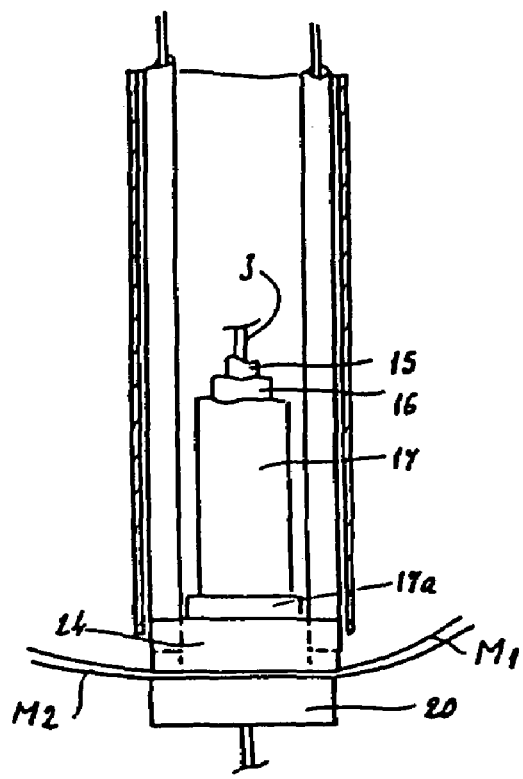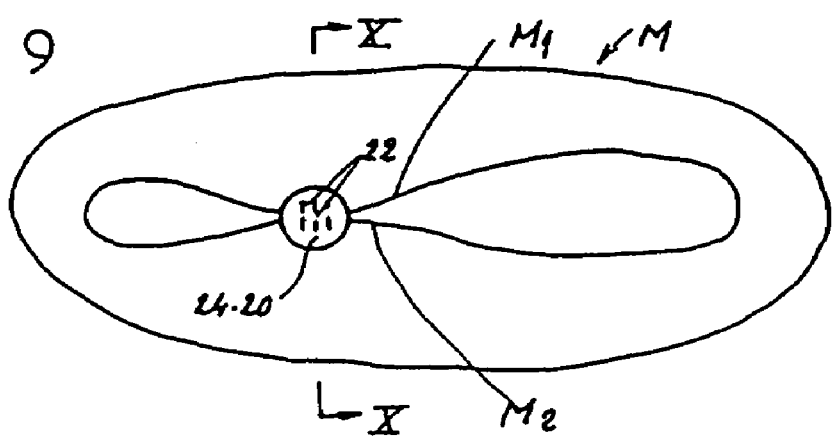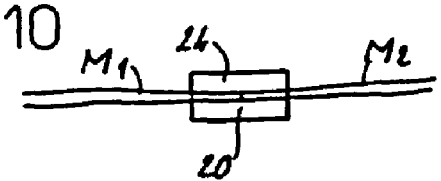

SURGICAL DEVICE FOR CONNECTING SOFT TISSUE

CROSS-REFERENCES TO RELATED APPLICATIONS

This application is a divisional of U.S. patent application Ser. No. 10/202,599 filed Jul. 24, 2002 now U.S. Pat. No. 6,770,083, which was a divisional of U.S. patent application Ser. No. 09/523,018, filed Mar. 10, 2000, now U.S. Pat. No. 6,461,366 which was continuation of PCT/FR98/01960, which designated the United States, filed Sep. 14, 1998, the full disclosure of which is incorporated herein by reference.

BACKGROUND OF THE INVENTION

This invention provides a surgical device allowing the percutaneous connection of two soft tissue areas that are ordinarily separate. This device is particularly intended for reconstruction of heart valves, especially the mitral valve, and for the treatment of any malformation of a heart septum.

In a condition known as mitral insufficiency, the mitral valve does not completely shut, and does not prevent the back-flow of blood to the left atrium from the left ventricle. Surgical repair is then necessary. In a current procedure, a sternotomy is performed. The patient is then placed under extra-corporal blood circulation while the heart is stopped, and the heart chambers are opened to gain access to the mitral valve, usually through the left atrium. Once the mitral valve is accessed, repair procedures include annuloplasty and, more recently, suturing of the free edge of the anterior leaflet to the free edge of the back leaflet where the mitral insufficiency occurs.

These procedures are complicated and require general anesthesia, sternotomy and extra-corporal blood circulation. They also require high doses of anti-coagulant therapy adding to the operative risk of a myocardial infarction and hemorrhage.

SUMMARY OF THE INVENTION

The methods of the present invention are performed percutaneously, diminishing considerably these risks. A surgical device allows the connection of two zones of soft tissue that are usually separate. In a particular embodiment, a connection is formed between a free edge area of an anterior mitral leaflet and a free edge area of a back mitral leaflet. Suitable surgical devices for performing tissue connection are described for example in EP 558 031 and WO 94/18893, and may comprise:

(a) a tube which may be inserted percutaneously until its distal extremity reaches the area around the tissues to be connected; and (b) two elongated elements inside that tube, each of which comprises a distal extremity having a device that grasps one of the two tissues to be connected;

(c) wherein the distal extremities of these elongated elements may be opened and closed in order to permit introduction into the desired area, allow the procedure.

Particular devices according to the present invention may further comprise:

(a) a grasping element, optionally having two parts for capturing each of the tissues to be connected, wherein the grasping or hooking element effects the connection of the two zones of tissue when brought close thereto by shifting of the portions of distal extremities to a position where they meet;

(b) a rod connected to each of the grasping or hooking elements and operated from the proximal end of the tube in order to axially shift the elongated element, wherein the rod can be separated from the grasping or hooking element upon pulling beyond a given threshold; and (c) a wedge inside the tube, allowing the axial immobilization of each grasping or hooking element while pulling on them.

The rod positions the insertion of the hooking element up to the level of the tissue edges to be connected. The rod also engages the hooking element against the wedge in order to open the two hooking parts.

According to the present invention, the device may be used to remotely grasp through a percutaneous passage, to draw together, and to connect the two zones of tissue by a simple external manipulation.

Preferably, the tube, the elongated elements, and the rod are flexible enough to be inserted percutaneously and through a patient's vasculature for the treatment of the leaflets of a cardiac valve, in particular the mitral valve. Each of the elongated elements is made out of an elastically flexible material, and one of these elongated elements diverges from the longitudinal axis of the other. The two elongated elements can move axially in relation to the tube between (a) a retracted position within the tube where the ends of the elongated elements are flexibly bent and closed together, and (b) a position where the ends of the elongated elements spring open and diverge from each other in a way that permits those ends to capture the soft tissues in order to grasp them.

The elongated elements may be deployed to allow their distal extremities to grasp the tissue areas or may be retracted in order to make the insertion, shifting or removal of the apparatus easier. Each elongated element may comprise a rod made of elastic material, with a curved distal extremity and/or a harpoon shape, and a sheath able to slide axially in a forward position to cover the distal extremity and slide back to uncover it.

According to a variation, each elongated element can be composed of a tube linked to a system that contracts its internal volume in order to grasp the corresponding tissue area, and expands to release the tissue with no lesion. In this case, the wide-mouthed shape of the elongated element's distal extremity will insure a large enough grasping surface.

Preferably, the device includes two hooking elements. One is operated on the distal side of the tissues, and the other, to be operated on the proximal side of the tissues, is situated between the first hooking element and the wedge element. This way the two hooking elements can be operated on both sides of the tissues and can be pressed together for a perfect attachment of those tissues.

BRIEF DESCRIPTION OF THE DRAWINGS

For greater clarity, the invention is described again in reference to the enclosed Figures representing two unrestricted examples of the invention in its optimal capacity.

FIG. 7 and FIG. 8 are similar views to FIG. 5 at different stages of the procedure.

FIG. 9 is a similar view to FIG. 2 of the mitral valve after treatment with the device.

FIG. 10 is a view of this valve according to line X-X of FIG. 9.

DESCRIPTION OF THE SPECIFIC EMBODIMENTS

Figure 1:
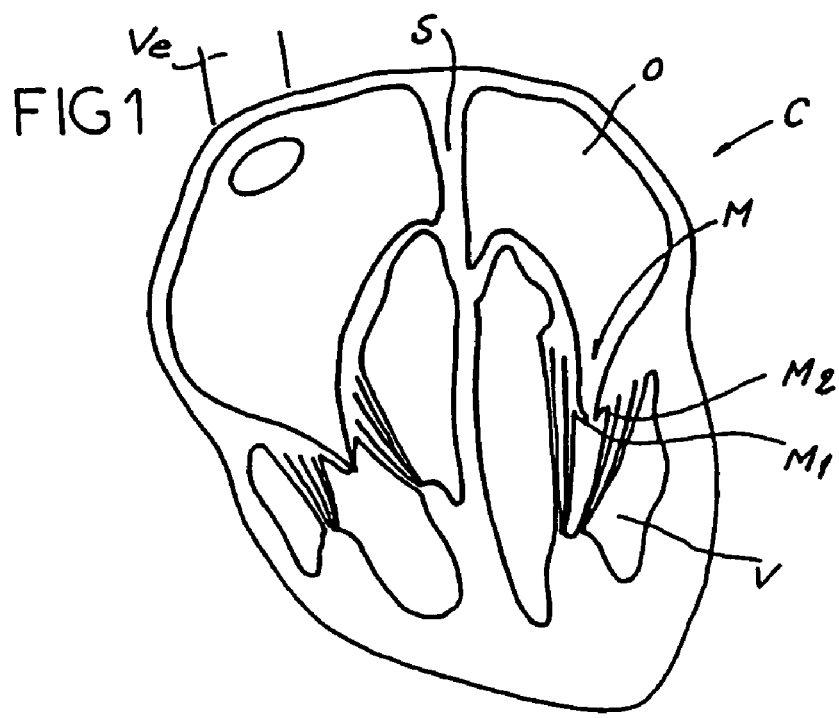
FIG. 1 shows a longitudinal section of a heart with a mitral valve that does not shut properly and has to be treated with this device.
Figure 2:
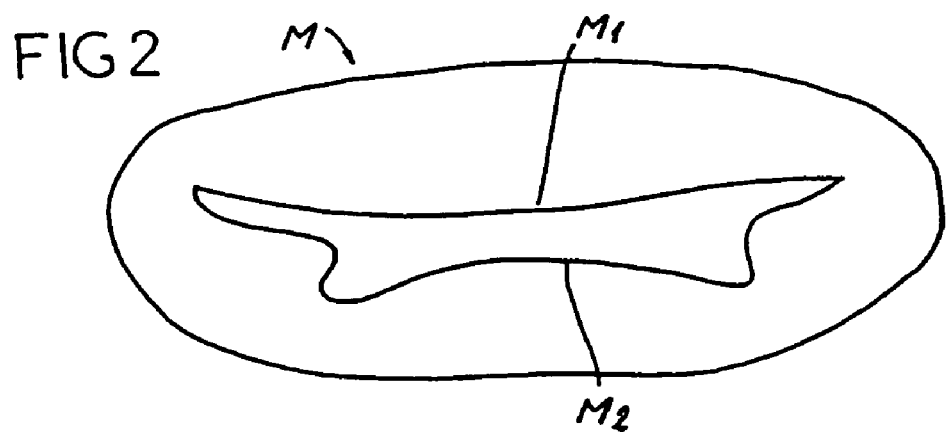
FIG. 2 shows the mitral valve before treatment.
Figure 3:
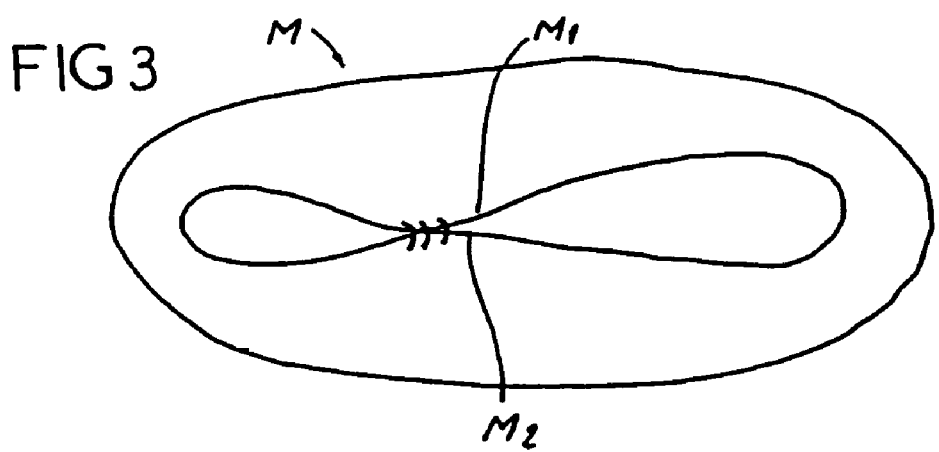
FIG. 3 shows a mitral valve similar to FIG. 2 after treatment by suture according to the usual procedure.

FIG. 1 shows a heart C with a mitral valve M having poorly opposed leaflets (M1, M2). Thus, the valve M does not shut tightly and no longer performs its back-flow function between the left atrium O and the left ventricle V. According to conventional procedures, after sternotomy, the patient is placed under extra-corporal blood circulation. The heart is stopped and the heart chambers are opened to directly reach to the valve M and stitch together the free opposite edges of both leaflets (M1, M2) as shown on FIGS. 2 and 3. Connecting leaflets M1 to M2 restores a good attachment between them and restores the imperviousness of valve M.

Figure 4:
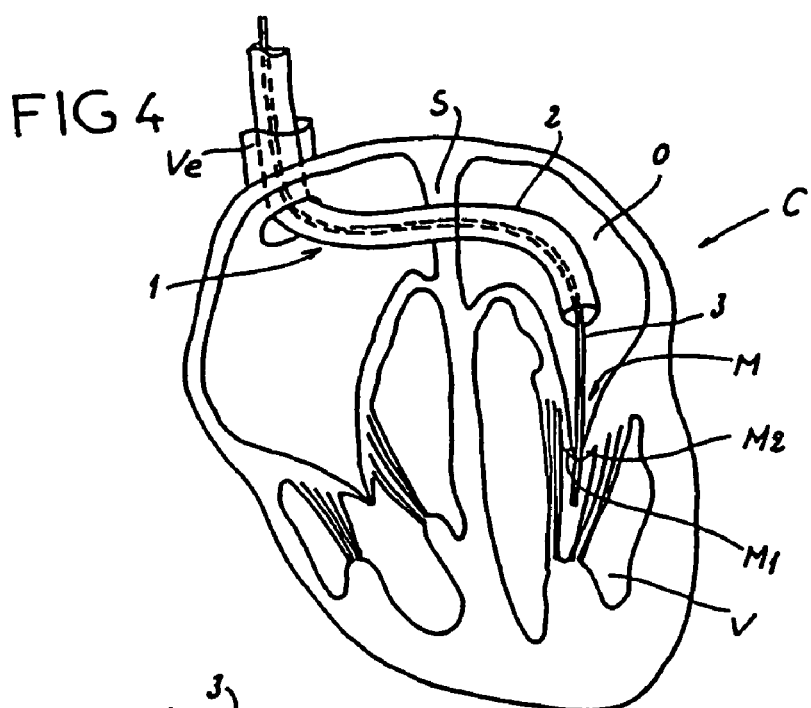
FIG. 4 is a view similar to that of FIG. 1, with the device of the present invention inserted into a heart.
Figure 5:
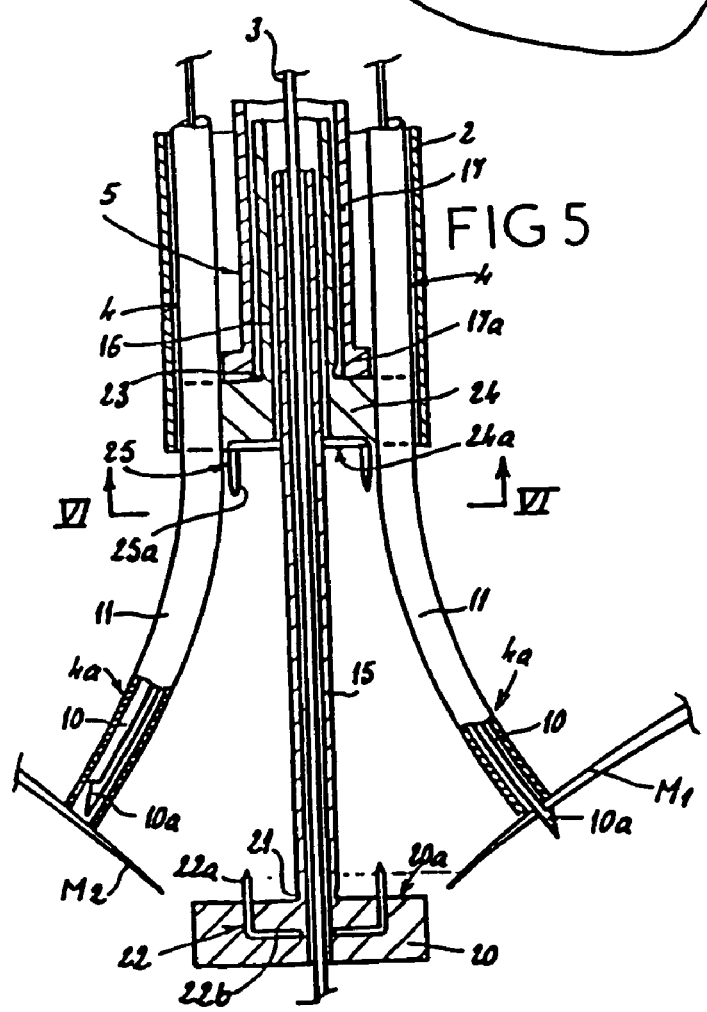
FIG. 5 is an enlarged view of a longitudinal section of the distal extremity of the device.

FIGS. 4 to 5 show a device (1) according to the present invention which enables the percutaneous connection of leaflet M1 to leaflet M2. This device (1) comprises an external tube (2), guidewire (3), two elongated elements (4), and a clipping system (5). The apparatus is sufficiently flexible to be percutaneously inserted into the heart C, through the patient's vascular, e.g., the Vena Cava Ve and the intra-atrial septum S. Guidewire (3) is inserted through valve M and so the distal extremity of external tube (2) is located in the left atrium O, with its distal opening facing mitral valve M.

Each of the elongated elements (4) has a distal extremity (4a) that is normally curved to diverge outwardly. A rod (10) is made out of a relatively rigid but still elastic material, more particularly in metal, with a sheath (11) of synthetic material. The distal extremity (10a) of the rod (10) is sharp and more or less harpoon-shaped. The sheath (11) fits on the rod (10) and can slide axially to a forward position (as shown on left side of FIG. 5) in order to cover the distal extremity of the rod, and can slide back (as shown on the right side of FIG. 5) in order to uncover that same distal extremity (10a). The elongated elements (4) extend from the end of the tube (2). Because of this, they can be shifted axially in relation to the tube (2) between a retracted position where the extremities (10a) close together (FIGS. 7 and 8) and an extended position where these same extremities (10a) diverge from each other (FIG. 5). The clipping system (5) comprises three concentric tubular rods (15, 16, 17) that can be slidably introduced over the guidewire (3). Each rod can also slide axially in relation to the others. The internal rod (15) is linked to a disk (20) through a frangible area (21). The rod and disk (15 and 20) are made of molded synthetic material. The disk (20) is axially pierced in order to let the guidewire (3) pass through, and carries a clip (22). Side prongs (22a) of that clip extend from the proximal face (20a) of the disk (20). A central portion (22b) of the clip (22) having a central ring for receiving the guidewire (3) is embedded into the material of the disk (24).

Figure 6:
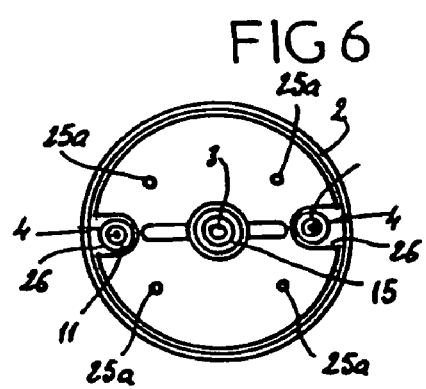
FIG. 6 shows a view of this distal extremity according to the line VI-VI of FIG. 5.

The intermediate rod (16) is also connected by a frangible area (23) to a disk (24) with two clips (25). Side prongs (25a) of these clips extend from the distal face (24a) of this disk (24), and central portions of the prongs are embedded into the material of the disk (24). On each side, the disk (24) has two diametrically opposed notches (26, FIG. 6) to allow the passage of the elongated elements (4). The external rod (17) has an expanded distal extremity (17a) which engages the proximal face of the disk (24). Each of these rods (15, 16, 17) can be extended beyond the proximal extremity of tube (2) so they can be shifted by the operator.

A handle or other structure for manipulating the rods (15, 16, 17) will usually be provided at a proximal end of the device. The handle will permit deployment rod (15) while rod (17) is held in a desired position in relation to tube (2), and then deployment rod (16), while rod (17) is also held in the desired position in relation to tube (2).

In practice, under X-ray or echography control, the guidewire (3) is first inserted through Vena Cava Ve, the intra-atrial septum S, and mitral valve M. Then tube (2) and its internal parts are inserted into the Vena Cava Ve and through the septum S until the distal extremity of tube (2) is directed at mitral valve M (FIG. 4). At this stage, disk (20) should be held at the opening of tube 2 (FIG. 5), while elongate elements (4) are retracted so that their distal extremities are retracted into slots (26).

When the distal extremity of tube (2) is in the proper position, rod (15) is shifted to advance disk (20) beyond leaflets M1 and M2 and into the left ventricle V. Elongate elements (4) are then advanced to their extended positions, as shown in FIG. 5. As the elongate elements (4) are advanced, their distal extremities diverge. After the elements (4) are advanced, distal extremities (10a) of rods (10) are positioned close to leaflets (M1, M2). The sheaths (11) of elements (4) are then retracted in relation to the rods (10) in order to uncover the extremities (10a), each of which can then pierce and capture the adjacent leaflet M1 or M2. Tube (2) is then advanced over the elongate elements (4), drawing the distal extremities (4a) closer, as shown on FIG. 7. This action draws the free edges of leaflets M1 and M2 together.

Rod (17) is advanced distally in relation to tube (2), and rod (15) is pulled proximally in relation to tube (2) in order to insert the prongs (22a and 25a) of clips (22 and 25) into the leaflets M1 and M2. The tension on rod (15) forces the prongs (22a and 25a) against the opposed walls (20a, 24a) of the disks (20, 24) and breaks frangible area (21). This break gives the prongs of the clips enough freedom of movement to ensure a good connection between leaflets M1 and M2. The sheaths (11) are then advanced distally in relation to the rods (10) to engage leaflets (M1, M2). This facilitates the extremities (10a) of the rods from the leaflets (M1, M2). Rod (16) is then pulled while holding rod (17) in position to break frangible area (25). Leaflets (M1, M2) have thus been clipped to each other by their free edges, as shown in FIGS. 9 and 10.

Figure 11:
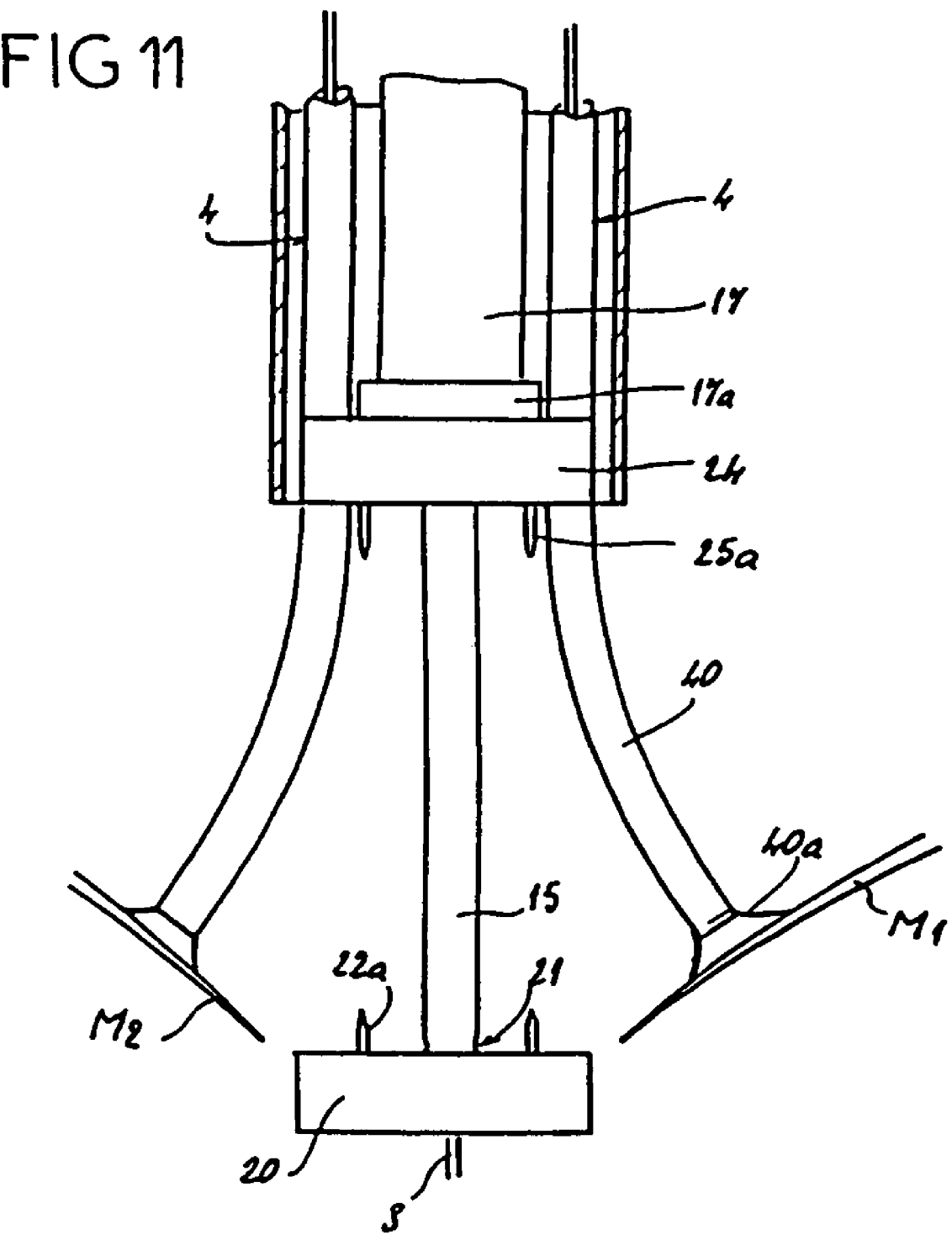
FIG. 11 illustrates an alternative embodiment of the device of the present invention.

FIG. 11 shows a variation of the apparatus where rods (10) and sheaths (11) have been replaced by two catheters (40) having trumpeted distal extremities (40a). These catheters (40) project beyond the proximal end of tube (2) and may be attached to syringes that permit the creation of negative pressure. The grasping or releasing of leaflets (M1, M2) is then achieved by controlling the internal pressure within catheters (40). The trumpeted ends (40a) ensure a sufficient grip on leaflets (M1, M2). Those ends (40a) are preferably sufficiently flexible enough to bend slightly when they are drawn between the wall of tube (2) and two lateral slots (26) of disk (20). The other parts of this alternative device are the same as already described and bear the same record numbers.

It goes without saying that the invention is not limited to the above example and is opened to different variations. For instance, the unstressed shape of the extremities (10a) that hook the tissues could be of a curved J which is straightened when drawn into the sheaths (11). The elongated parts (4) and the connecting system could also be placed in separate tubes. The device (1) could be inserted arterially as well as veinously.

What is claimed is:

1. A system for performing cardiac valve repair, said system comprising:
   a tube suitable for introducing through a patient's vasculature and into a chamber of a heart; and
   a clipping system including a first pair of elements adapted to be brought up beneath a pair of valve leaflets from the ventricular side and a second pair of elements adapted to be brought down over the pair of valve leaflets from the atrial side, wherein the first pair of elements engages the ventricular side of both leaflets and the second pair of element engages the atrial side of both the leaflets to capture both leaflets and wherein the first and second elements may be left to attach the free edges of the leaflets together.

2. A system as in claim 1, wherein the first pair of elements and the second pair of elements comprise prongs.

3. A system as in claim 2, wherein the first pair of prongs project toward the second pair of prongs.

4. A system as in claim 3, wherein the prongs penetrate leaflets held therebetween.

5. A system as in claim 1, further comprising a pair of elongate elements extensible from a distal end of the external tube, wherein each element is adapted to capture a valve leaflet.

6. A system as in claim 5 wherein the elongate elements are spring-biased to diverge outwardly when advanced distally relative to the external tube.

7. A system as in claim 5, wherein each elongate element has a distal extremity adapted to capture a valve leaflet.

* * * * *